United States Patent [19]

Blough

[11] Patent Number: 4,603,122

[45] Date of Patent: Jul. 29, 1986

[54] ANTIVIRAL AGENT AGAINST HERPES VIRUS INFECTIONS

[76] Inventor: Herbert A. Blough, 4119 Kottler Dr., Lafayette Hill, Pa. 19444

[21] Appl. No.: 345,487

[22] Filed: Feb. 3, 1982

Related U.S. Application Data

[63] Continuation-in-part of Ser. No. 67,504, Aug. 17, 1979, Pat. No. 4,315,001.

[51] Int. Cl.$^4$ .............................................. A61K 31/70
[52] U.S. Cl. ...................................................... 514/23
[58] Field of Search ...................... 424/180; 536/1.1; 514/23

[56] References Cited

U.S. PATENT DOCUMENTS 4,315,001  2/1982  Blough ................................ 536/1.1

OTHER PUBLICATIONS

Courtney et al., "Chem. Abst.", vol. 81, 1974, p. 146286s.
Ludwig et al., "Chem. Abst.", vol. 83, 1975, p145392c.
Gallaher et al., "Chem. Abst.", vol. 79, 1973, p122293z.
Courtney, "Chem. Abst.", vol. 85, 1976, p137934g.
Iwasaka et al., "Chem. Abst." vol. 90, 1979, p. 115793.
Kilbourne, "Nature", vol. 183, pp. 271–272, 1959.
Ray et al., "The Lancet", Sep. 1974, pp. 680–683.
Goodhart et al., "The New England Journal of Medicine" Jun. 7, 1979, p. 1338.
Blough, et al., "Jour. of the American Medical Assn.", Jun. 29, 1979, vol. 241 #26.

*Primary Examiner*—Johnnie R. Brown
*Attorney, Agent, or Firm*—Ralph T. Lilore

[57] ABSTRACT

A method of treating herpes virus infections by the administration of 2-deoxy-D-glucose is described. The sugar analog is effective in treating herpes simplex virus infections such as, genital herpes, labial herpes, and ocular herpes; and other herpes infections such as, herpes zoster, varicella, mononucleosis, erythema multiforme and cytomegalovirus.

6 Claims, No Drawings

ANTIVIRAL AGENT AGAINST HERPES VIRUS INFECTIONS

This application is a continuation-in-part of my co-pending application Ser. No. 67,504, filed Aug. 17, 1979, now U.S. Pat. No. 4,315,001.

The present invention relates to a method of treating herpes virus infections. In particular, a method is described for the effective treatment of herpes simplex derived diseases such as, genital herpes, labial herpes and ocular herpes, and other herpes caused infections such as, herpes zoster, herpes varicella (chicken pox) and mononucleosis (caused by the so-called Epstein-Barr virus, a herpes virus). Two types of herpes simplex virus (HSV) have been described in the literature. They are generally referred to as type 1 and type 2. The predominant clinical manifestation of type 1 is recurrent herpes labialis (cold sores) and corneal infections (keratitis). Type 2 in humans is primarily associated with recurrent herpetic vulvovaginitis (in women) and penile lesions in men.

Herpes simplex virus, types 1 and 2, account for approximately 500,000 new cases of venereal disease each year, and there are approximately 13 to 15 million sufferers of this disease in the United States alone. Genital herpes simplex infection is characterized by severe pain followed by the appearance of blisters (vesicles) which may coalesce to form large blebes. When the symptoms are allowed to go untreated the virus may then migrate to the deeper tissues of the body such as the lymph nodes and neural tissues resulting in lymphadenopathy, which may be tender, and problems which simulate sciatic nerve neuralgia. In many cases the infection is accompanied by systemic effects such as fever, listlessness, and a "washed-out" feeling. In addition, the virus may spread to the fetus at the time of delivery (causing encephalitis). The virus infection is also believed to have a relationship to cancer of the cervix.

Herpex zoster (shingles) is an acute infection of the central nervous system, is extremely painful and is characterized by the appearance of typical vesicular eruptions and neuralgic pain in cutaneous areas supplied by the peripheral sensory nerves. Most often the eruptions appear in the thoracic region. Post herpetic neuralgia often results with prolonged pain of months to year often involved.

Varicella (chicken pox) is often theorized to be the juvenile form of zoster, the latter tending to occur in adults rather than in children. Typical vesicles are associated with the disease as are the itching, pain and discomfort normally encountered with herpes lesions.

Mononucleosis, though now considered a herpes infection caused by the Epstein-Barr virus, does not usually have herpes-type vesicles associated with it, although the commonly encountered lymphadenopathy seen in other herpes infections is also seen here. Generally, the disease manifests itself in vague flu-like symptoms often with C.N.S. involvement, i.e., headache, meningeal irritation and neuritic pain. The course of the disease can be protacted with prolonged periods (months) of pain, discomfort and incapacitation. Enlargement and tenderness of spleen and liver are common and characteristic.

The relationship between the herpes viruses and encephalitis and Kaposi's Sarcoma and Kaposi's varicelliform eruptions should not be overlooked. These are potentially serious diseases for which effective therapy is aggressively sought. At the moment there are relatively few and only sporadically effectiveness modes of treatment for herpes infections. Currently, treatment of mononucleosis, zoster, varicella, genital and labial herpes involves merely reducing symptoms.

Treatment for herpetic infections in other parts of the body, such as the eye, for example, has involved the use of various nucleoside derivatives such as, adenine arabinoside and trifluoromethylthymidine. Treatment of genital lesions has involved the use of dyes and photodynamic inactivation. Smallpox vaccine, BCG (Bacillus Calmette-Guerin) and influenza virus vaccine have been used intradermally in the treatment of genital herpes, but none of the known methods has proved to be satisfactory in treating disease.

It has now been determined that the glucose analog 2-deoxy-D-glucose is effective as a chemotherapeutic agent in the treatment of herpes simplex and other herpes infections. 2-deoxy-D-glucose is a simple sugar molecule which is found in many lower organisms. It can be obtained from plants and other eukaryotic cells. It is colorless and stable in aqueous solutions.

The present invention, therefore, provides a safe and convenient method of treating genital herpes, labial herpes, herpes keratitis with uveitis; herpes zoster, varicella, mononucleosis, erythema multiforme and cytomegalovirus.

DESCRIPTION OF PREFERRED EMBODIMENTS

The approach to the treatment of genital and labial herpes virus infections has, in general, been restricted to the use of those agents that inhibit synthesis of or interact with viral nucleic acids, namely, 5-iodo-2'deoxyuridine, 9-$\beta$-D-arbinofuranosyladenine, and 5-trifluoromethyl-2'-deoxyuridine, as well as photodynamic inactivation using intercalating agents such as acriflavine or proflavine followed by white (visible) light. All these compouonds have been proved to be totally ineffective in the treatment of genital herpes and herpes uveitis and in other herpes infections. Furthermore, the possibility exists that the photodynamically inactivated virus has an enhanced oncogenic potential. Many of the antiviral drugs interfere with DNA metabolism and are potential mutagens; alternatively, persons may be sensitized with the emergence of a resistant population of virions. 2-deoxy-D-glucose is a relatively non-toxic compound that is administered in a simple fashion and penetrates rapidly into most tissues, depending upon the vehicle employed, and when used intravaginally or intrarectally is rapidly absorbed systemically.

The antiviral action of 2-deoxy-D-glucose has been known for 20 years, but its clinical use has not been explored. The metabolism of 2-deoxy-D-glucose has been reviewed. 2-deoxy-D-glucose is incorporated directly into glycoproteins and glycolipids and appears to block the cellular synthesis of the major glycosylated polypeptide of the herpes virus. For example, in HSV-infected cells treated with 2-deoxy-D-glucose, hematosides are notably reduced, with an accumulation of precursor molecules, namely, the ceramide backbone. In addition, 2-deoxy-D-glucose appears to prevent the synthesis and transport of nonstructural glycolipids. 2-Deoxy-D-glucose, therefore, is a rational and effective chemotherapetic agent in the treatment of genital herpes because of its ability to prevent the synethesis of macromolecules required for the envelope biogenesis and recognition phenomenon. Although 2-deoxy-D- glucose shows a unique efficacy in the treatment of genital herpes, it has also been found to be effective for the treatment of labial or oral herpes as well as ocular herpes and for the treatment of herpes zoster, varicella, mononucleosis, erythema multiforme and cytomegalovirus.

For use in treating herpes infections, 2-deoxy-D-glucose is formulated in a pharmaceutically acceptable, non-irritating vehicle. The vehicle may be in any suitable form such as a lotion, cream, oil or emulsion or it may be formulated into a rectal or urethral suppository. Suitable pharmaceutically acceptable vehicles include polyethylene glycol, mineral oil, petrolatum, propylene glycol, glycerol and the like or a buffered acid jelly. The sugar analogue may be used alone or in conjunction with a fungicide such as miconazole nitrate, miconazole or mylostatin. The fungicide serves as a control of fungal growth. The formulated sugar is then applied topically to the infected area and treatment is continued until the lesion is healed. It is preferred, however, that the treatment be systemic and most preferably that the drug be administered orally (enteric coating), intravaginally or rectally. The amount of 2-deoxy-D-glucose employed in the formulation is generally between 10 mmole and 125 mmole per day in divided doses. The preferred range is 12 mmole to 50 mmole. When used in the form of a suppository, the suppository is compounded with about 3 mg to 20 mg of 2-deoxy-D-glucose. For labial or oral herpes about 10 mmole to 25 mmole of 2-deoxy-D-glucose is used (per day). For zoster varicella and mononucleosis the dose range is conveniently 75 to 200 mg per day in divided doses. Preferably the drug is given four times per day rectally for about 2 weeks.

The invention may be illustrated as follows: Thirty-six women with genital herpes infections (proved by virological or cytological means) were treated in a double-blind placebo-controlled study with 2-deoxy-D-glucose for a three-week period. Of the cases reported in this series, 10% were type 1, and 90% were type 2. Tissue culture was positive for HSV in all cases (both placebo- and 2-deoxy-D-glucose-treated cases) except one; in the latter, diagnosis was made by cytological examination. Sixty-five percent of all women, either placebo or 2-deoxy-D-glucose treated, had concomitant positive cervical cultures. Colposcopy followed by cytological examination, namely, examination for giant cells, was positive in 10% of all cases. The following five mixed infections were encountered; two with *Trichomonas vaginalis;* two with *Candidia albicans,* and one patient with HSV and both trichomonas and monilial infections. Gonorrhea and syphilis were not seen in this group. Herpesvirus serological examination offered little to the diagnostic regiment except in those cases where an anammestic response was encountered.

Patients with initial infections treated with 2-deoxy-D-glucose had a rapid relief of pain and dysuria (the two most common complaints occurring in 100% and 70%, respectively) within 12 to 72 hours vs eight to ten days in those receiving placebo treatment. Therapy with 2-deoxy-D-glucose substantially decreased the duration of lesions after initiation of therapy (Table 1). With initial mucocutaneous cases, both the lesions and subjective symptoms persisted 60% longer in the placebo-treated controls than in the 2-deoxy-D-glucose-treated patients. In placebo-treated cases, the number of lesions frequently remained the same or increased, and in a few of these, they progressed to extensive coalescent or excoriating lesions that involved the entire anogenital region as well as tender lymphadenopathy. In contrast those successfully treated with 2-deoxy-D-glucose had a more rapid devolution of symptoms and progressive lesions were not observed. In 2-deoxy-D-glucose-treated initial patients, lesions became negative for HSV within four days compared with 15 days for placebo-treated controls (Table 1); the earliest negative culture following 2-deoxy-D-glucose treatment was 24 hours.

In the case of recurrent infections, response was immediate after the institution of 2-deoxy-D-glucose. The duration of the lesions following therapy in this group was approximately half of that observed in placebo-treated patients ($P<0.011$), and virus shedding was reduced (Table 1). The clinical course of placebo-treated controls was the same as that of the untreated population (with recurrent genital herpes). Deoxyglucose treatment reduced or prevented recurrence in both initial and recurrent cases (Table 2). During a 2 two-year period, among all patients with initial HSV treated with 2-deoxy-D-glucose, there were two recurrences. The recurrence rate averaged 35% to 40% in this study as well as in a subselected population of eight patients with initial disease treated with miconazole only. Among the 2-deoxy-D-glucose-treated patients with recurrent infections, eight patients had no recurrence, eight had fewer exacerbations, and the remaining two failed to respond to therapy. The latter two patients had been previously treated by photodynamic inactivation. No resistant strains emerged during the course of 2-deoxy-D-glucose therapy, and no untoward reactions to 2-deoxy-D-glucose were encountered.

TABLE 1

Effect of 2-Deoxy-D-Glucose on Genital Herpesvirus Infection*

| Therapy Used | Duration of Lesion Following Therapy, Days** | Duration of Positive Viral Culture Following Treatment, Day** |
|---|---|---|
| Initial Placebo | 18.0 ± 3.00 | 15.3 ± 2.52 |
| 2-Deoxy-D-glucose | 8.2 ± 0.90 | 4.3 ± 0.53 |
| P | <.001 | <.001 |
| Recurrent Placebo | 12.0 ± 1.00 | 15.3 ± 2.50 |
| 2-Deoxy-D-glucose | 6.8 ± 0.6 | 4.4 ± 0.46 |
| P | <.001 | <.001 |

*Patients were treated topically with 2-deoxy-D-glucose in a vehicle or with a placebo (vehicle alone or vehicle plus D-glucose).
**Number of days ± SEM.

TABLE 2

Efficacy of 2-Deoxy-D-Glucose vs Placebo Therapy on Recurrence of Genital Herpes

| Therapeutic Regimen | No Recurrence, % | Decreased Frequency of Recurrences, % | Unfavorable Response Based on Recurrent Rate, %* |
|---|---|---|---|
| Initial | | | |
| Without 2-deoxy-D-glucose (n = 8)** | 65 | Not Applicable | 31 |
| With 2-deoxy-D-glucose (n = 18)*** | 89 | Not Applicable | 11 |
| P | <.001 | — | — |
| Recurrent Disease**** | | | |
| Without | 0 | 0 | 100 |

TABLE 2-continued

Efficacy of 2-Deoxy-D-Glucose vs Placebo Therapy on Recurrence of Genital Herpes

| Therapeutic Regimen | No Recurrence, % | Decreased Frequency of Recurrences, % | Unfavorable Response Based on Recurrent Rate, %* |
|---|---|---|---|
| 2-deoxy-D-glucose (n = 7)** | | | |
| With 2-deoxy-D-glucose (n = 18)*** | 45 | 45 | 10 |

*A 10% rate for recurrent disease with 2-deoxy-D-glucose refers to no change in either severity or frequency.
**Patients treated with vehicle alone or vehicle plus D-glucose.
***Patients treated with 2-deoxy-D-glucose.
****For recurrent disease in 90% of the patients with a favorable Response P<.001.

For labial herpes, the treatment consisted of the application of 2 to 3 drops of a 50 millimolar solution of 2-deoxy-D-glucose in sterile anhydrous glycerol. Lesions epitheliazed in 4–5 days with complete healing within a week. Symptoms of pain, salivation, and swelling abated in 48 hours.

For ocular herpes, the treatment consisted of the application of 2 to 3 drops of a 20 or 50 millimolar solution of 2-deoxy-D-glucose in sterile anhydrous glycerol applied every three hours during the waking period. Difficult lesions such as herpetic ulcers at the limpus epitheliazed in four days. Vision frequently 20/100–20/200, returned to normal levels within five days. Herpetic uveitis responded equally as well to the treatment with 2-deoxy-D-glucose.

The following are examples of formulations containing 2-deoxy-D-glucose:

A. Miconazole Nitrate Cream with 2-Deoxy-D-glucose Procedure for 3000 g
1. Add the 2-Deoxy-D-glucose to a portion of the formula Purified Water and mix until solution is effected.
   2-Deoxy-D-glucose: 5.25 g
2. Place the MONISTAT-7 Cream into a stainless steel mixing bowl.
   MONISTAT-7: 2970.0 g
3. Slowly add the 2-Deoxy-D-glucose solution to the cream in the mixing bowl.
4. Rinse the vessel containing the solution of 2-Deoxy-D-Glucose with the remainder of the formula Purified Water and add to the cream in the mixing bowl. Mix until uniform using a planetary mixer. The total amount of Purified Water used is 24.75 g.

B. Cream with 2-Deoxy-D-glucose
Procedure for 3000 g
1. Add the 2-Deoxy-D-glucose to a portion of the formula Purified Water and mix until solution is effected.
   2-Deoxy-D-glucose: 5.25 g
2. Place the Placebo Cream Vehicle into a stainless steel mixing bowl.
   Placebo Cream Vehicle: 2970.0g
3. Slowly add the 2-deoxy-D-glucose solution to the cream in the mixing bowl.
4. Rinse the vessel containing the solution of 2-deoxy-D-glucose with the remainder of the formula Purified Water and add to the cream in the mixing bowl. Mix until uniform using a planetary mixer. The total amount of Purified Water used is 24.75 g.

C. Placebo Cream
Procedure for 3000 g
Place the following into a stainless steel vessel.
Placebo Cream Vehicle: 2970.0 g
Purified Water, USP: 30.0 g
Mix until uniform using a planetary mixer.

D. Alternative Method of Preparing Monistat Formulation

One milliliter of a 500 mM aqueous solution of 2-deoxy-D-glucose is added to 47 gm of a base consisting of:
mineral oil
pagoxal 7-sterate
peglicol 5-oleate
butylated hydroxyanisole
benzoic acid and water
in a 50 ml syringe. The mixture is mixed by rapid swirling using a glass rod or pipette. After mixing, the contents of the syringe are forced directly into an aluminum tube which is lined with plastic for application in the infected area.

In addition, special suppositories made of the monistat vehicle in which is compounded 3 mg of 2-deoxy-D-glucose can be made in one of two ways. Either the 2-deoxy-D-glucose can be made prior to the hardening of the suppository into solidified state or alternatively the suppositories can be drilled and filled with a cream containing monistat vehicle in the equivalent of 3 mg of 2-deoxy-D-glucose. In all cases these are weighed and ascertained for biological activity and for the presence of the active ingredient by gas liquid or thin layer chromotography.

Treatment of other herpes infections such as those caused by zoster, varicella and EB Virus (Epstein-Barr) is indicated by the following:

Seven patients, (3 with confirmed diagnosed mononucleosis and 4 with confirmed herpex zoster) were treated rectally with 2-deoxy-D-glucose daily as indicated below. The active compound was provided in the form of a cream as described heretofore under Formulations A and B. The cream was applied with a rectal applicator. All patients responded quickly to therapy. In all cases systemic response could be measured by the quantification of blood levels of 2-deoxy-D-glucose. In the case of infectious mononucleosis, the clinical response was very dramatic, with fever and hepatosplenomegaly (enlarged liver and spleen) quickly resolving. Fever was virtually gone within three days; blood chemistries reverted rapidly to normal, and there was only minimal fatigue at the end of the course of therapy.

In the case of herpes zoster, even more dramatic results were obtained. Pain was relieved within 24–48 hours; lesions cleared slowly over two weeks, but the itching and post-herpetic neuritis commonly seen with zoster was rapidly alleviated following therapy again with 75–150 mg of 2-deoxy-D-glucose q.d. in divided doses (per rectum). The healing time of lesions was approximately one-half that of the untreated population.

Patient No. 1 had symptoms characteristic of herpes zoster as follows: There were visible zoster vesicles on the left-side anterior portion of the chest just below the breast. There was no involvement of additional dermatomes. Lab data indicated that she was negative for varicella and herpex simplex virus. She complained of burning and some pruritus. Therapy was commenced at a level of 23 mg per day divided into 3 doses for 3 days administered rectally as were the others. There was slow response initally. The dose was then increased to 75 mg per day divided into 3 doses resulting in rapid resolution of symptoms including the absence of post-herpetic neuralgia, a very unusual and desired end result in zoster patients. The lesions disappeared within 10 days after the commencement of therapy with no residual post-herpetic neuritis. Therapy continued for 2 weeks from the date of first administration. Disappearance of lesions in untreated zoster patients normally does not take place until about 3 weeks after onset.

Patient No. 2 presented with an early stage of herpes zoster on the upper torso with involvement on the left thorax. He complained of burning and itching. 2-deoxy-D-glucose therapy was started at a level of 46 mg per day divided into 4 doses for about 3 weeks. Immediately after taking the drug the patient claimed relief from symptoms with minimal itching and no residual burning. Following treatment there was no post-herpetic neuralgia.

Patient No. 3 was a male who developed shingles and had a problem with urination because of involvement of the neurons which supply the bladder. Urination was impossible without the use of a catheter and there was tenderness between the legs and on the left side of his buttocks extending into the genital area. 2-deoxy-D-glucose therapy with 75 mg per day, 4 doses per day for 2 weeks, was begun. Within 7 days the catheter was removed, and the patient was voiding well. The patient was totally asymptomatic when therapy was discontinued.

Patient No. 4 presented with a vesicular rash at the C3 to C5 dermatomes. She had fever, malaise and viremia and complained of an intermittent searing pain along the C3 dermatome. This pain initially started in the back of the neck and radiated down along the dermatome. It became totally incapacitating to the point that hospitalization was required. The deep neuralgia associated with this condition was not responsive to fairly heavy doses of demerol and several stellate ganglion blocks. The patient was then started on 2-deoxy-D-glucose at a level of 75 mg per day divided into 4 doses. Within 24 hours there was complete resolution of the deep incapacitating neuralgia with only a slight burning and surface pain being felt. The patient was on therapy for 14 days and at that point the herpes zoster condition was resolving. This patient also had positive titer for varicella.

Patient No. 5 had confirmed symptoms of mononucleosis having positive liver enzymes and positive heterophiles. He complained of a sore throat and weakness and had a temperature of 103°. Therapy with 2-deoxy-D-glucose was started at a total of 75 mg per day divided into three doses of 25 mg each. Within 5 hours after therapy began, the sore throat disappeared, and his pain was markedly reduced. He had a marked increase of strength. Within 24 hours his pallor was markedly reduced, and he had a good appetite. His temperature, which had been 103°, returned to normal within 2 days. Three days after institution of therapy, he was back attending college as a full-time student. Laboratory studies indicated that his clinical chemistries reverted to normal within 1 week after the institution of therapy. His relative lymphocytosis of 72% reverted to 31% within 14 days after therapy was started.

Patient No. 6 was positive for mononucleosis as determined by both a commercial mononucleosis test, and by examination of the clinical chemistry enzymes. Commencement of 2-deoxy-D-glucose therapy was started at 70 mg per day divided into 4 doses. Within 10 days of treatment, there were no nodes detectible, and the patient's throat was normal. Treatment was discontinued after 11 days. At the end of three weeks, the commercial test for mono was negative, and the SGPT enzyme was normal.

Patient No. 7 had clinical symptoms of slight fever, nausea and swollen glands. Her tonsils were enlarged and marked with exudate. A commercial test for mononucleosis was positive. When 2-deoxy-D-glucose therapy was started the patient's temperature was 102°, and she had a palpable tender liver and a palpable tender spleen. Within 1 day of treatment her temperature had gone down to 100° there was tiredness, but less pain in swallowing. Within 3 days her temperature was down to 98°-99°. The glands were smaller and nontender. The spleen was nonpalpable, and her appetite was good. Within 6 days after treatment the patient stated that she felt great. Within 1 week after therapy was commenced, her tonsils were only slightly enlarged, and by the end of 17 days after therapy was commenced her findings were normal. The therapy used in this case was 35 mg per day divided into 4 doses per day for the first 7 days then 75 mg per day, 4 doses per day, for the next 10 days, then 37.5 mg per day for the next day, then 22.5 mg per day for 5 days then 15 mg for the next 2 days.

Eight patients (5 males and 3 females) with herpes simplex caused erythema multiforme (EM) were treated with 2-deoxy-D-glucose rectally and vaginally as appropriate. Active compound dose levels were in the range of 75 to 170 mg per day in 4 divided doses. Vesicles began to resolve within 2 days and substantial relief from pain, burning and itching was obtained. As is known, EM involves the production of lesions on the skin especially on fingers, chest, face and legs etc., as a result of sensitization by herpes antigens and is extremely painful and disabling. Therapy in accordance with the present invention removes the objectionable symptoms much faster than is normally obtained in untreated patients. Often times these lesions fail to recur in contrast to untreated patients who can expect fairly frequent recurrences.

Since the time period for the appearance of EM (sensitization) is 7-14 days after onset of active herpes virus infection or sensitization, by a vaccine for example, the 2-deoxy-D-glucose can be used prophylactically to prevent this complication or therapeutically.

What is claimed is:

1. A method for treating herpes virus infections in a human patient which comprises treating said patient with a composition comprising an amount of 2-Deoxy-D-Glucose which is effective against herpes zoster, herpes varicella or mononucleosis, in a pharmaceutically acceptable carrier.

2. The method of claim 1 wherein the patient is treated by administering the 2-deoxy-D-glucose systemically.

3. The method of claim 2 wherein the patient is treated intravaginally, topically or rectally.

4. The method of claim 1 wherein the amount of 2-deoxy-D-glucose used is between 50 and 225 mg per day.

5. The method of claim 4 wherein an antifungal agent is additionally present.

6. The method of claim 5 wherein the antifungal agent is miconazole nitrate.

* * * * *